(12) United States Patent
Cordaro et al.

(10) Patent No.: US 7,695,497 B2
(45) Date of Patent: Apr. 13, 2010

(54) IMPLANT SYSTEM FOR OSTEOSYNTHESIS (75) Inventors: Nicholas M. Cordaro, Oceanside, CA (US); Colin M. Smith, Dana Point, CA (US)

(73) Assignee: SeaSpine, Inc., Vista, CA (US)

( * ) Notice: Subject to any disclaimer, the term of this patent is extended or adjusted under 35 U.S.C. 154(b) by 1028 days.

(21) Appl. No.: 11/224,443

(22) Filed: Sep. 12, 2005

(65) Prior Publication Data
US 2007/0073291 A1 Mar. 29, 2007

(51) Int. Cl.
A61B 17/70 (2006.01)

(52) U.S. Cl. .................. 606/267; 606/266; 606/268

(58) Field of Classification Search .................. 606/61, 606/72–73, 99, 246, 254, 257, 267, 270
See application file for complete search history.

(56) References Cited

U.S. PATENT DOCUMENTS

| 5,005,562 A | 4/1991 | Cotrel |
|---|---|---|
| 5,154,719 A | 10/1992 | Cotrel |
| 5,261,912 A | 11/1993 | Frigg |
| 5,385,583 A | 1/1995 | Cotrel |
| 5,536,268 A | 7/1996 | Griss |
| 5,667,508 A | 9/1997 | Errico et al. |
| 5,752,957 A | 5/1998 | Ralph et al. |
| 5,782,833 A | 7/1998 | Haider |
| 5,882,350 A | 3/1999 | Ralph et al. |
| 5,885,286 A | 3/1999 | Sherman et al. |
| 5,989,254 A | 11/1999 | Katz |
| 6,261,287 B1 | 7/2001 | Metz-Stavenhagen |
| 6,302,888 B1 | 10/2001 | Mellinger et al. |
| 6,440,137 B1 | 8/2002 | Horvath et al. |
| 6,565,567 B1 | 5/2003 | Haider |
| 6,620,163 B1 * | 9/2003 | Michelson ............... 606/286 |
| 6,660,006 B2 * | 12/2003 | Markworth et al. ......... 606/61 |
| 6,837,889 B2 | 1/2005 | Shluzas |
| 2001/0023350 A1 * | 9/2001 | Choi ........................ 606/61 |
| 2003/0153911 A1 | 8/2003 | Shluzas |
| 2004/0138660 A1 * | 7/2004 | Serhan ...................... 606/61 |
| 2004/0147936 A1 | 7/2004 | Rosenberg et al. |
| 2004/0267264 A1 | 12/2004 | Konieczynski et al. |

* cited by examiner

*Primary Examiner*—Eduardo C Robert
*Assistant Examiner*—Elana B Fisher (57) ABSTRACT

A anti-splay and rod securing member for use with vertebral implants of the hook, monoaxial and polyaxial types, in which a pair of arcuate upstanding internally threaded posts define a transverse opening for securing a rod to immobilize bone segments comprises an integrally formed cap and set screw with the cap having opposed curved side walls extending around the posts and flat end walls, the set screw being positioned within the posts and free to rotate within the cap so that rotation of the set screw will advance the cap and set screw in unison along the implant posts to clamp the rod and implant together. The implant may be provided with opposed catch basins for releasably securing the distal end of a rod persuasion instrument.

26 Claims, 11 Drawing Sheets

IMPLANT SYSTEM FOR OSTEOSYNTHESIS

FIELD OF THE INVENTION

The present invention relates to the medical field commonly referred to as Osteosynthesis, i.e., the fusion between segments of the spine and more particularly to an implant system for use with a rod for immobilizing the segments during the fusion process.

BACKGROUND OF THE INVENTION

Osteosynthesis is achieved by immobilizing separate bone segments and in particular vertebral segments on either side of a failed or damaged disc. When trying to achieve osteosynthesis and specifically fusion between different segments of the spine, one has to provide some type of immobilization. There are various prior art systems which try to achieve this purpose. The different systems involve placement of implants in the form of hooks secured against the bone or pedicle screws threaded into the bone. The implants are then secured to each other by stabilizing rods or plates.

Figure 1:
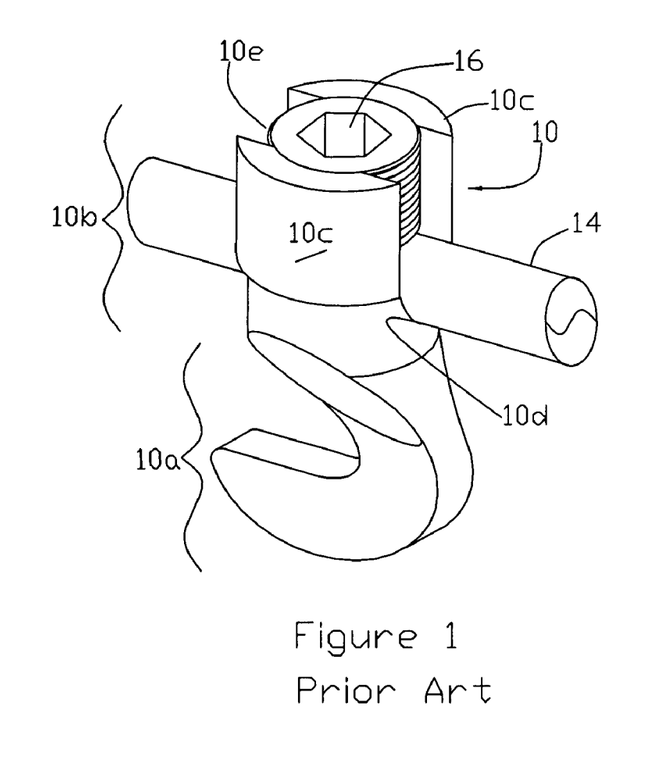
FIG. 1 is a perspective view of a prior art hook implant and securing set screw.

A typical prior art hook implant system, illustrated in FIG. 1, includes a hook implant 10 having a bottom section 10a in the form of a hook shaped finger to be mounted on a bone segment and an upper rod receiving section 10b having a pair of internally threaded posts 10c extending upwardly from a generally unshaped rod receiving cradle or chamber 10d. The posts define a transverse opening 10e for receiving a stabilizing rod 14. A plug 16, e.g., a set screw, having external threads complementary to the internal threads in the posts, completes the system. The set screw, when tightened, clamps the rod and the hook implant together. The term "hook implant", as used herein, refers to the type of hook 10 illustrated in FIG. 1.

Figure 2:
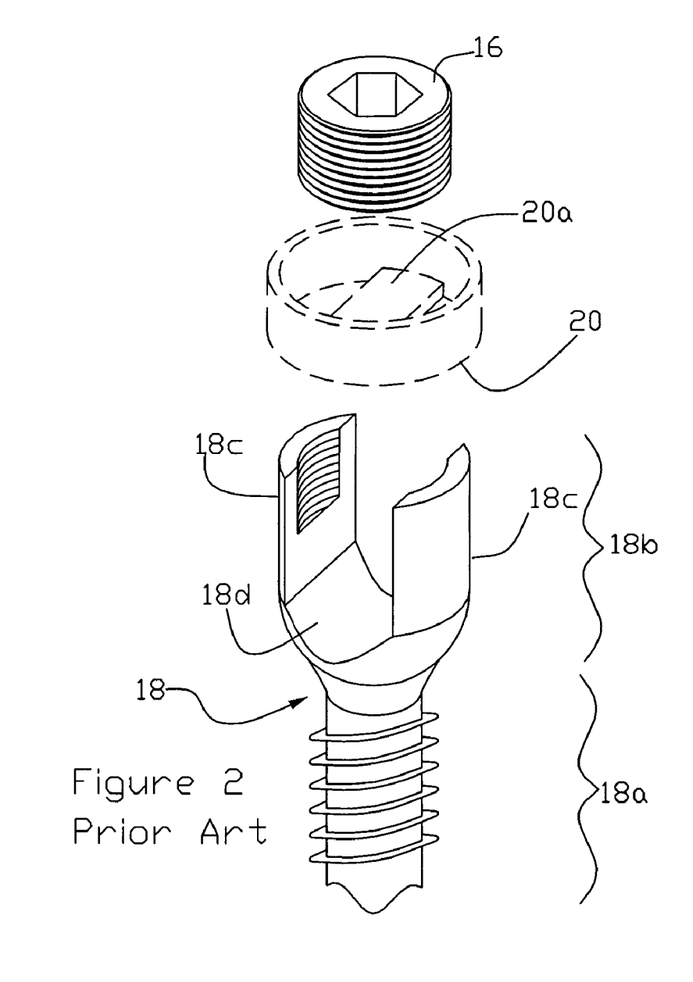
FIG. 2 is a perspective unassembled view of a prior art monoaxial screw implant with a securing set screw and an antisplaying ring (in dotted lines)

Another type of typical prior art implant for use with a stabilizing rod, commonly referred to as a monoaxial pedicle screw, is illustrated in FIG. 2. The implant 18 consists of a bottom section, in the form of a threaded shaft 18a, joined to an upper rod receiving section 18b formed by a pair of opposed internally threaded posts or branches 18c extending upwardly from a cradle 18d. A threaded plug, e.g., a set screw 16, when threaded into the posts, clamps the implant and rod together. The term monoaxial pedicle screw as used herein refers to the type of implant illustrated in FIG. 2. The monoaxial pedicle screw implant system may include an anti-splay ring 20 (shown in dashed lines) extending around the posts and supporting a flat or curved plate 20a below the set screw so that the plate is forced against the rod by the advancing screw. See, for example, U.S. Pat. Nos. 5,154,719 and 5,385,583.

Figure 3A:
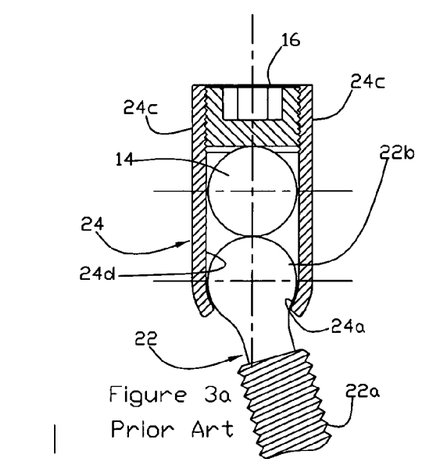
FIGS. 3a and 3b are cross-sectional and side elevational views, respectively, of a prior art polyaxial pedicle screw implant and securing set screw.
Figure 3B:
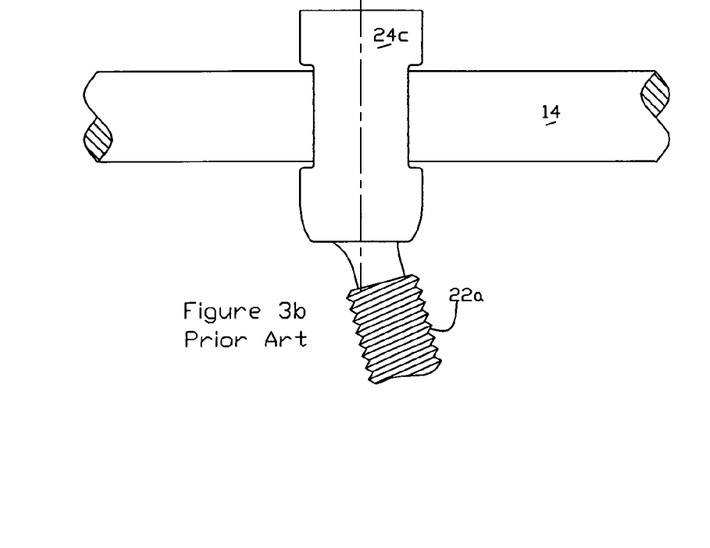
Figure 4:
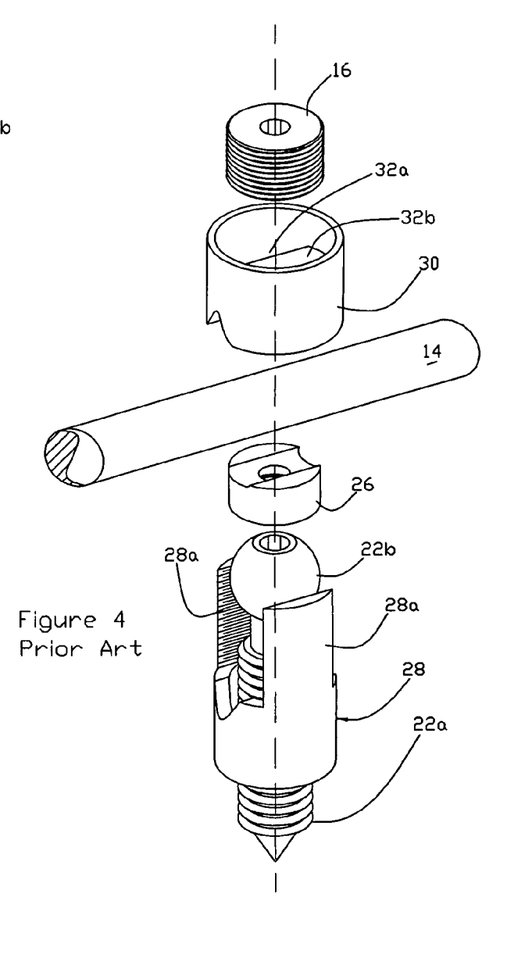
FIG. 4 is an unassembled perspective view of a prior art polyaxial pedicle screw with a securing set screw, an antisplaying cap and a pressure washer.

A prior art implant, initially providing several degrees of freedom between the rod receiving portion of the implant (upper section) and the portion (bottom section) secured to the bone, is commonly referred to as a polyaxial pedicle screw. An implant system employing a polyaxial screw is illustrated in FIGS. 3a and 3b in which the threaded shaft 22a of the bone screw 20 is inserted through a longitudinal opening in a cage or housing 24 with the enlarged head 22b of the screw resting against a reduced cross-sectional area 24c of the housing. The housing, like the upper section of the monoaxial housing, has opposed upstanding internally threaded posts 24c which define a transverse opening or slot 24d for receiving the rod. A set screw 16, when tightened, forces the rod against the head of the screw to clamp the rod, housing and bone screw together. Prior to tightening the set screw the housing may be pivoted relative to the head of the bone screw. See U.S. Pat. No. 6,261,287 and FIGS. 15 and 16. A more advanced polyaxial screw system is shown in FIG. 4 and described in U.S. Pat. No. 6,565,567 in which a pressure washer 26 (initially vertically moveable relative to the housing 28) is placed between the rod and the head 22b of the bone screw 22. The '567 implant system also includes a cap 30 with openings 32a which slide over the posts 28a and a lower lateral connector 32b interposed between the bottom of the set screw 16 and the rod 14.

The term polyaxial pedicle screw as used herein refers to implants of the types shown in FIGS. 3a, 3b and FIG. 4 minus the set screw and cap.

The caps or rings which extend around the internally threaded posts in certain of the above implants serve the purpose of limiting or preventing the outward deflection or splaying of the posts as the set screw is tightened. However, the use of such a cap or ring along with a separate set screw requires two separate steps on the part of the surgeon, i.e., first inserting the cap over the posts and second placing the set screw between posts so that the threads are properly aligned. The step of aligning the set screw with the threaded posts is a problem whether or not a separate cap is used. Since the threads in the posts are interrupted it is difficult, particularly in light of the limited view in the surgical opening for a surgeon to ensure that the set screw is not canted with respect to the opening in the posts, resulting in cross threading and likely a failed installation.

There have been several attempts, by way of patent disclosures, to overcome these problems. See, for example, U.S. Pat. Nos. 5,261,912 ("'912 patent"), 5,667,508 ("'508 patent"), 5,752,957 ("'957 patent") and 6,440,137 ("'137 patent"). All of such patents teach the use of a unitary locking cap having a male threaded plug or set screw (adapted to be received in the threaded posts) with the cap forming a concentric rim joined to the top of the plug. While this arrangement solves the multiple component problem it presents another problem of raising the vertical profile of the installed implant. The extra space required to accommodate the top of the clamp, which necessarily overlies the top of the implant posts, may result in considerable discomfort to a tall, thin patient particularly if the implant is installed in the thorax region. It is preferable to keep the vertical profile of the implant as short as possible.

In addition, the above unitary cap/screw designs do not entirely solve the screw/threaded posts alignment problem. Such arrangements may tend to allow the cap/screw to pivot or toggle slightly along the openings between the implant posts.

A feature of the present invention is directed towards a solution to such problems by providing an integrally formed cap and set screw with the set screw free to rotate within the cap and the cap/set screw defining means for aligning the set screw with the implant posts. Preferably, the cap defines diametrically opposed openings which slide over the posts with the ends of the openings cooperating with the posts' edges to guide the cap/set screw into alignment with the longitudinal axis of the implant.

In addition to the separate component and alignment problems, conventional implants systems suffer another problem. It is necessary to seat the stabilization rod between the implant posts. This seating step is frequently difficult due to the rigidity of the rod and the vertebra into which the implant has been installed, particularly where the vertebrae is to be moved toward the rod.

To aid the surgeon in accomplishing this task, implants are typically provided with opposed generally cylindrical recesses or slots in the upper section, generally below the rod receiving cradle. A rod persuasion instrument or persuader, in the form of an elongated carriage member, has spaced arms at its distal end which are arranged to slide into the slots or arms provided with inwardly extending flexible fingers arranged to snap into the recesses to releasably fix the distal end relative to the implant. A shaft slidably mounted in the carriage member and actuable from the proximal end (i.e., located exterior of the patient's body) allows the surgeon to push the rod into the receiving chamber in the implant and retain it in that position while the set screw or other clamping means is threaded into the implant posts to lock the rod and implant together. See, for example, U.S. Pat. No. 6,660,006 ("'006 patent") and U.S. Patent Publication No. US2004/0147936 A1 ("'936 publication). The arms of the '936 device are offset and slide into opposed slots in the upper section below the cradle. This persuader design requires that adjacent implants be at least as far apart as the transverse/offset arms at the distal end of the instrument thereby limiting its use to adjacent implants with the required spacing. In addition, it is difficult to align and slide the offset arms into the slots.

The implant grasping arms at the distal end of the '006 persuader, enclosed within a sleeve or cannula, are flexed outwardly to allow the inwardly projecting fingers to clear the sides of an implant. The arms then snap inwardly to allow the fingers to snap into the recesses at the implant base. The distal end of the cannula is then moved forwardly to retain the fingers within the implant recesses. This arrangement, like the '936 device, also limits the persuader's use on closely spaced adjacent implants. In addition, the securing set screw must be passed through the length of cannula before entering the threaded posts of the implant.

A feature of the present invention, whether of the hook, monoaxial or polyaxial pedicle screw type, overcomes such shortcomings by providing opposed flat recessed sides along the base of the upper section of the implant, aligned with the posts, with the recesses terminating at their upper ends in concave, e.g., outwardly projecting, shoulders.

This arrangement permits the use of a simple persuader which (a) accommodates a close spacing between adjacent implants, (b) eliminates the need for a releasably attachable arm/finger mechanism and (c) is user friendly in terms of placing the distal end of the persuader within the recesses.

Another feature of the present invention, applicable to hook or monoaxial implants, is the design of the cradle to accommodate stabilizing rods of different diameters by providing the cradle with different radii.

With respect to polyaxial screws, a feature of the present invention is to provide a pressure washer with the rod receiving cradle having a slightly smaller radius than the radius of the rod so that the upper edges of the cradle are internally forced outwardly by the rod to create an interference fit. The pressure washer is also preferably made of a material such as a CoCvMo alloy, which has a hardness value about 15% to 22% greater than the hardness value of titanium. The increased hardness of the washer provides a better locking interface between the underside spherical sector of the washer and the screw head thereby requiring less force to secure the rod, polyaxial housing and the pedicle screw together. It is noted that the '567 patent indicates that heat treating titanium may increase the hardness value by about 10% to 20%. However, tests have shown heat treatment actually increases the hardness value by only one or two points on the Rockwell C hardness scale or about 5% or less.

SUMMARY OF THE INVENTION

An improved anti-splay and rod securing member for use with vertebral implants of the hook, monoaxial and polyaxial types, in which a pair of arcuate upstanding internally threaded posts define a transverse opening for securing a rod to immobilize bone segments comprises (a) a cap having opposed curved side walls adapted to extend around the posts and preferably substantially flat end walls extending between the side walls, with the cap and posts having cooperating means to coaxially align the cap with the posts and (b) a set screw mounted in the cap to be positioned within the posts and having a top wrench engaging surface, a bottom and external threads arranged to engage the post threads. The cap and set screw are formed as an integral unit with the set screw being free to rotate within the cap so that rotation of the set screw will advance the cap and set screw in unison along the implant posts. A lower portion of the cap or set screw is arranged to engage the rod to clamp the rod and implant together.

Preferably the cap includes at least one top and bottom strut extending between the end walls between which the set screw is encased. The bottom strut may be in the form of a concave rod-engaging surface, e.g., semi-cylindrical, saddle or u-shaped, so that when the set screw is advanced along the posts the lower strut engages the top of the rod. Alternatively, the lower strut may extend between one or both side walls leaving a portion of the bottom of the set screw free to engage the top of the rod.

In another embodiment, the upper rod holding section of an implant, whether of the hook, monoaxial or polyaxial pedicle screw type, may be provided with a flat opposed recessed sides, adjacent the bottom of the posts, with the recesses terminating at their upper ends in concave outwardly projecting shoulders. This arrangement, sometimes referred to herein as a catch basin, accommodates the use of a rod persuader having a fixed forked distal end, i.e., parallel arms, with inwardly projecting stubs adapted to slide under the shoulders to releasably secure the persuader distal end to the installed implant.

A rod persuasion instrument, for use with the above recessed sided implant, includes an elongated carriage member extending along a longitudinal axis with a proximal and distal end. A pair of spaced parallel arms are preferably offset at an acute angle to the longitudinal axis at the distal end with each arm having an inwardly projecting stub or button on the end thereof. The stubs are arranged to slid along the flat recessed sides and abut the concave shoulders to releasably fix the persuader distal end relative to the implant. A pusher bar is slidably mounted in the carriage member with a distal end having a concave surface for engaging the upper surface of the rod. The pusher bar is manually actuable via a rachet arrangement from the proximal end of the persuader to allow a surgeon to force the rod between the implant posts.

The construction, operation and features of the disclosed invention may best be understood by reference to the following description taken in conjunction with the appended drawings where like components are generally given the same reference numerals in the several figures.

DESCRIPTION OF THE PREFERRED EMBODIMENT

Figure 5A:
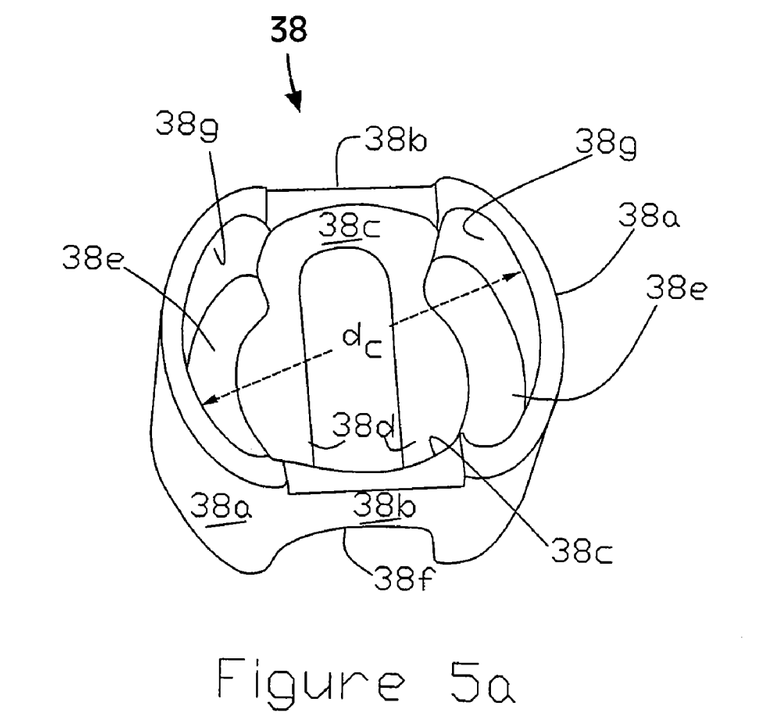
FIGS. 5a and 5b are perspective views of a partially complete cap and a set screw in an unassembled condition, in accordance with the present invention.
Figure 5B:
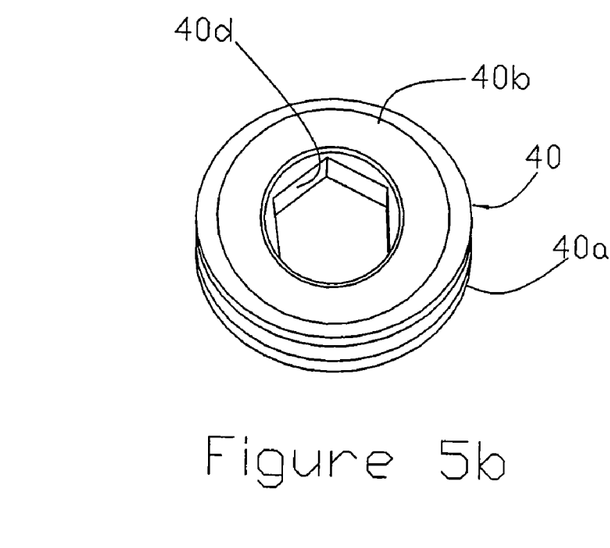
Figure 6A:
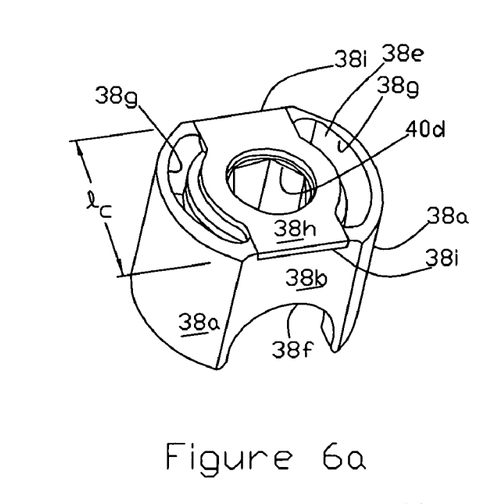
FIGS. 6a, 6b and 6c are top perspective, cross-sectional, and bottom perspective views, respectively, of an assembled cap/set screw in accordance with this invention for use with implants having upstanding internally threaded posts.

A partially completed cap 38 and a set screw 40 are illustrated in FIGS. 5a and 5b. The cap is manufactured from a high strength bio-compatible material such as titanium, e.g., by machining, a solid piece to provide opposed curved side walls 38a which are arranged to extend around and follow the outside contour of a generic implant's upstanding posts 36a (FIG. 6) leaving an open top. The implant posts have free edges 36b which are aligned parallel to the implant's longitudinal axis $X_I$-$X_I$. It is to be noted that the bottom section 36c of the generic implant of FIG. 7 may be of the hook, monoaxial or polyaxial type.

Figure 6B:
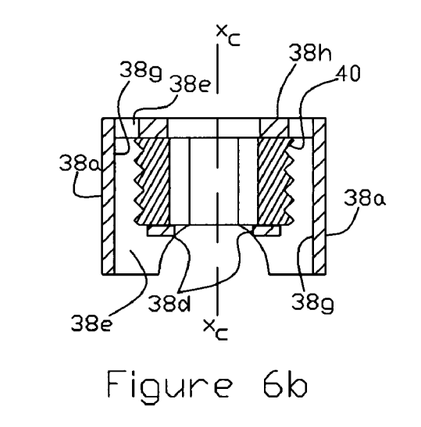
Figure 7:
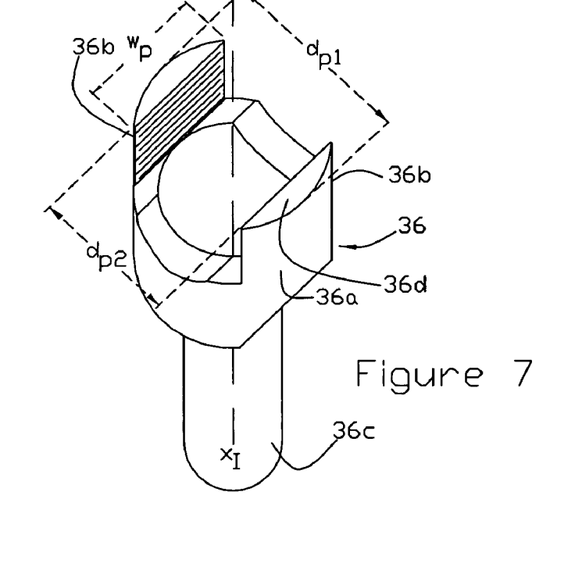
FIG. 7 is a perspective view of the top section of a generic implant adapted to receive the integral cap/set screw of the present invention.

Flat end walls 38b of the cap extend between the side walls, as shown, and along with the side walls are arranged to encircle the implant posts. The inner surfaces 38c of the end walls are contoured to match the outer circumference of the set screw with a slight clearance, e.g., 0.0005 to 0.010" to allow the set screw 40 to turn freely or with a slight resistance while aligning the set screw with the longitudinal axis Xc-Xc of the cap (FIG. 6b). A split bottom strut 38d extends across the bottom center section of the end walls leaving diametrically opposed openings 38e between the strut and the inner surface 38g of the side walls which serve to guide the cap onto the implant posts as will be explained. Each segment of the bottom strut 38d extends downwardly and outwardly along a radius generally following the contour of the rod 14. End walls 38b are formed with an upwardly concave surface 38f which, like the split strut, generally follow the contour of the rod.

The set screw 40 (with external threads 40a matching the post threads 36b) may then be inserted inside the cap where it is automatically aligned with the cap axis Xc which axis will be coincident with the longitudinal axis $X_I$-$X_I$ (FIG. 7) of the implant when the cap/set screw is inserted over the posts 36a. A top strut 38h (FIG. 6a) is then positioned across to the top of the end walls and welded thereto, for example, along lines 38i. The top strut provides diametrically opposed cutout openings (also 38e) aligned with the bottom openings. The cut out openings have a length lc (FIG. 6a).

The set screw 40, with its top surface 40b underlying the strut 38h and its bottom surface 40c overlying the split strut 38d, is thus positioned or encased within the cap while remaining free to rotate therein. The set screw is provided with a wrench engaging surface 40d, e.g., a hexagonal socket compatible with an allen wrench, accessible through a central aperture 38j and the top strut 38g.

The diameter dc of the inner curved surfaces 38g of the cap (FIG. 5a) is slightly greater, e.g., 0.0005" to 0.010" or 0.020" than the outside diameter $dp_1$ of the curved implant posts (FIG. 7) while the perimeter of the inside surfaces 38g are sized to be slightly larger, i.e., 0.001" to 0.010" or 0.020" than the perimeter of the outside surface of the posts. By the same token the length (lc) of each cutout or opening 38e (FIG. 6a) is just slightly greater than the width Wp of the posts (FIG. 7), e.g., 0.001 to 0.010" or 0.020". The upper limit for the above clearances is not to be considered limiting and in any event such clearances will depend to some extent on the size of the implant. This arrangement insures that when the cutouts formed by the side walls inner surfaces 38g and the strut at the bottom portion of the cap are slid over the implant posts, with the post edges cooperating with the ends of the cutouts, the set screw will be aligned with the posts threads thereby inhibiting any cross threading.

Figure 6C:
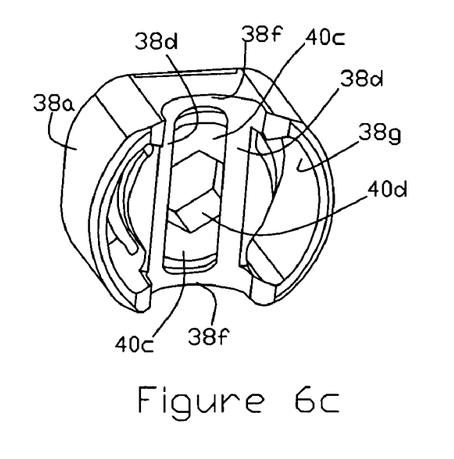

It is to be noted that while the end walls are illustrated as flat, they may be curved, e.g., matching the curvature of the side walls, with openings 38e and the posts edges or other cooperating means between the cap and posts (with or without a bottom strut) serving to prevent rotation of the cap with the set screw while guiding the cap/set screw into a coaxial alignment with the implant posts. Such cooperating means may include ribs extending inwardly from the cap inner walls which engage the posts edges or a tongue and groove arrangement between the cap side walls and the posts. The preferred embodiments are as shown in FIGS. 6 and 10 (to be described) with flat end walls and a bottom strut.

Figure 8A:
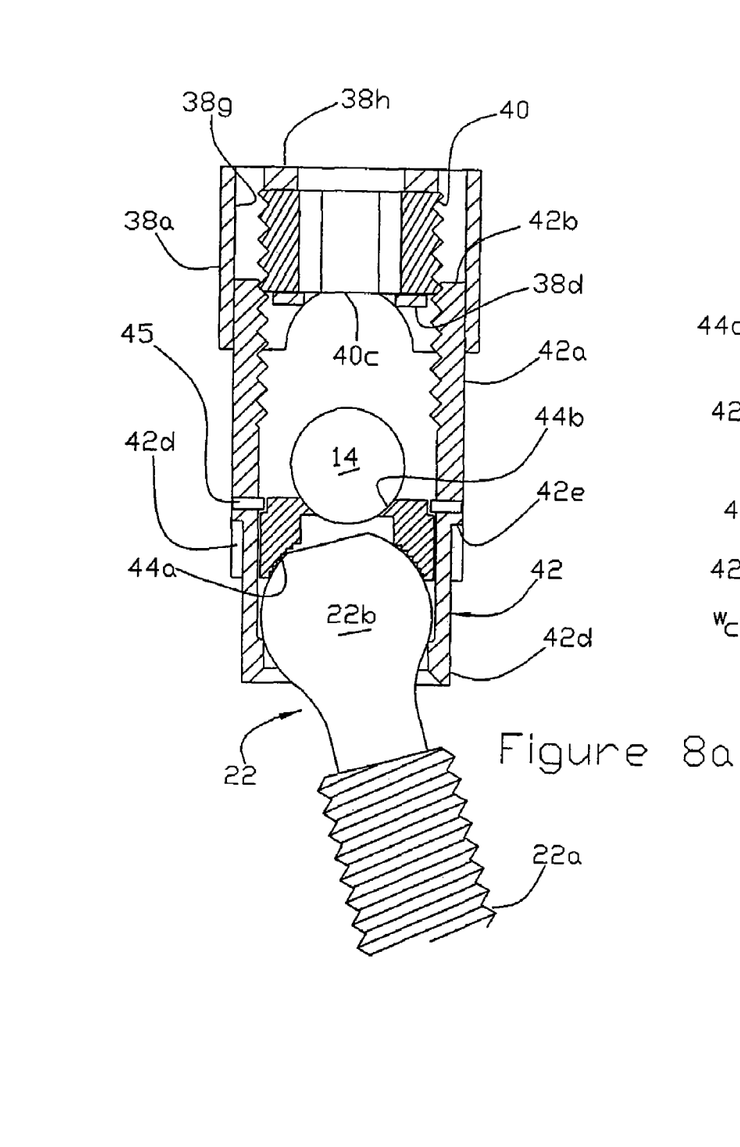
FIGS. 8a and 8b are cross-sectional views of the cap/set screw of FIG. 6 being installed on a polyaxial pedicle screw implant, illustrating how the openings between the bottom strut and the cap inner wall aid in guiding the set screw into the post threads.
Figure 8B:
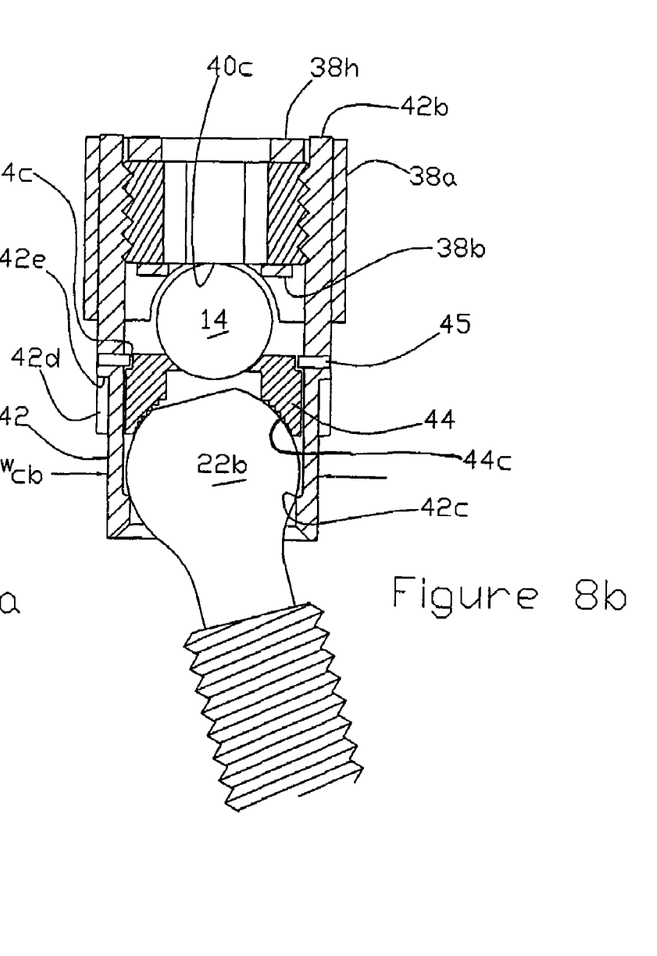

The manner in which the cap openings 38e and the implant posts, including the free edges thereof, serve to align the screw with the longitudinal axis of the implant is illustrated in FIGS. 8a and 8b in which the implant is in the form of a polyaxial pedicle screw with a housing 42 having internally threaded posts 42a terminating in top circular sector surfaces 42b. The head 22b of the bone screw 22 is positioned between a reduced cross section 42c of the housing and a pressure washer 44. FIG. 8a illustrates the initial engagement of the set screw threads with the posts threads after the lower cap openings 38e in cooperation with the post edges, adjacent the top surfaces 42b, have aligned the cap/set screw with respect to the housing longitudinal axis. FIG. 8b illustrates the set screw and cap in the installed position with the bottom surface 40c of the set screw forced against the rod 14 which in turn forces the washer against the pedicle screw head to lock the assembly together.

Figures 9A, 9B, 9C:
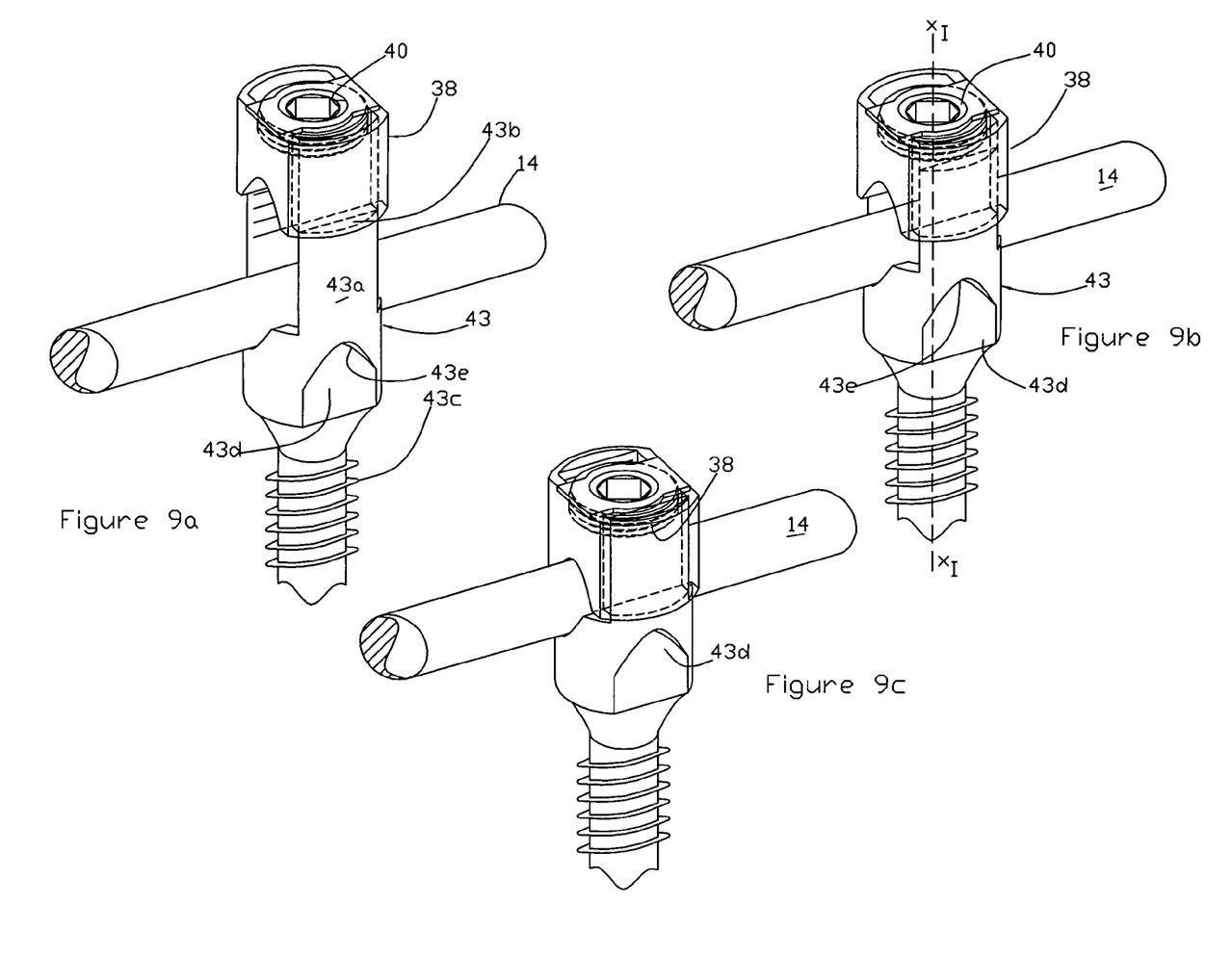
FIGS. 9a, 9b and 9c illustrate, in simplified perspective views, the installation of the cap/set screw of FIG. 6 on the upper section of a monoaxial pedicle screw.

FIGS. 9a, 9b and 9c illustrates the installation of the integrally formed cap/set screw 38 on a monoaxial pedicle screw 43 with upstanding internally threaded posts 43a. FIG. 9a shows the top of the implant posts entering the lower cap openings 38e to coaxially align the cap/set screw with the longitudinal axis $X_I$-$X_I$ of the implant. FIG. 9b shows the partial installment and FIG. 9c (like FIG. 8b) illustrates the cap/set screw in its final position.

It is to be noted that while FIGS. 8 and 9 illustrate the placement of the integrally formed cap/set screw over the posts of a polyaxial and monoaxial screw implant the integrally formed cap/set screw of the invention may be inserted over the posts of a hook implant.

As noted earlier, the preferred pressure washer 44 has a hardness value of about 10% to 25% (and preferably 15% to 22%) greater than the hardness value of the pedicle screw head. It has been found that a washer made of a cobalt chromium molybdenum alloy (CoCrMo) has a Rockwell C hardness value of around 43 as compared with a Rockwell C hardness value of around 35 for titanium. The increased hardness of the CoCrMo alloy serves to cause the ridges 44a of the underside of the pressure washer to bite into the pedicle screw head and ensure a superior locking arrangement. The washer has a partial cylindrical surface 44b on its upperside for engaging the rod. Preferably the radius of the surface 44b is slightly smaller than the radius of the rod to allow the sides of the washer creating the upper surface to be slightly spread apart by the rod creating a clamping action between the washer and rod. The washer is provided with diametrically opposed short vertical slots 44c, illustrated as being aligned with center of the posts. Pins 45, inserted through the side walls of the posts, extend into the slots to allow a small vertical movement of the washer while maintaining the surface 44b aligned along the transverse rod receiving opening.

An important feature of the present invention is a rod persuasion instrument catch basin which is formed by opposed flat recessed sides 42d on the polyaxial housing side walls (FIG. 8) or 43d on the upper section of the monoaxial implant (FIG. 9) with the recessed sides terminating at their upper ends in concave outwardly projecting shoulders 42e (FIG. 8) or 43e (FIG. 9) adjacent the bottom of the posts. The depth of the shoulders need to be sufficiently deep, e.g., about 0.4 mm to 3 mm and preferably about 2 mm, to serve as a catch for inwardly projecting stubs or buttons on a persuasion instrument described in connection with FIGS. 13a and 13b. For example, the outside diameter of the posts $dp_1$ (FIG. 7) may range from 0.012" to 0.55" depending upon the anticipated diameter of the stabilization rods. A typical outside diameter of 0.4528 with an inside diameter $dp_2$ (FIG. 7) of 0.2600 will readily accommodate rods having a diameter of 0.216" to 0.250". In any event, the width $W_{CB}$ (FIG. 8b) of the catch basin, i.e, recessed sides, will normally be the thinnest portion of the polyaxial housing or upper section of a hook or monoaxial pedicle screw implant. It is to be noted that while the catch basin is shown on the housing of a polyaxial pedicle screw implant (FIG. 8) and on a monoaxial pedicle screw implant (FIG. 9) it is equally applicable for use on the upper section of a hook implant.

Figure 10A:
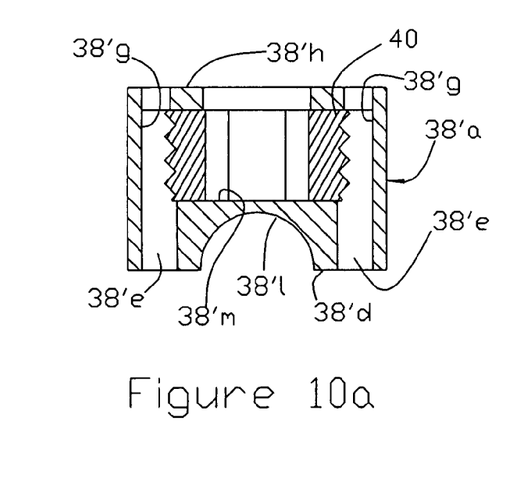
FIGS. 10a and 10b are cross-sectional and bottom views, respectively, of a modified cap/set screw.
Figure 10B:
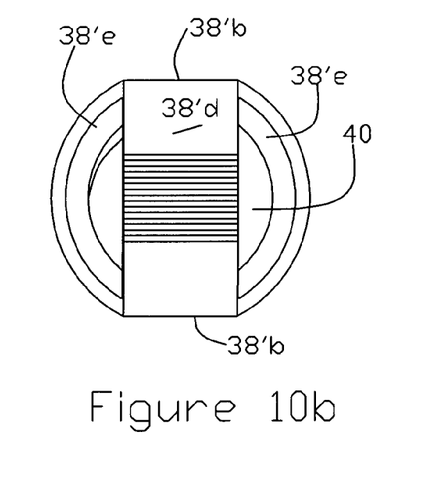

An alternative embodiment of an integrally formed cap 38'/set screw 40, in accordance with this invention, is illustrated in FIGS. 10a and 10b with the top of the cap/set screw being the same as that shown in FIG. 6a. The difference resides in the bottom strut 38'd (FIG. 11b) having a semi-cylindrical, saddle or u-shaped centrally disposed lower surface 38'l (generally following the contour of the rod) which extends between the end walls 38'b (marked 38b on FIG. 6a). The upper surface 38'm of the lower strut 38'd is substantially flat. As is illustrated in FIGS. 10a and 10b the diametrically opposed openings 38'e between the lower strut 38'd and the inner surfaces 38g of the cap side walls 38'a serve to guide and align the cap/set screw onto implant posts.

Figure 11A:
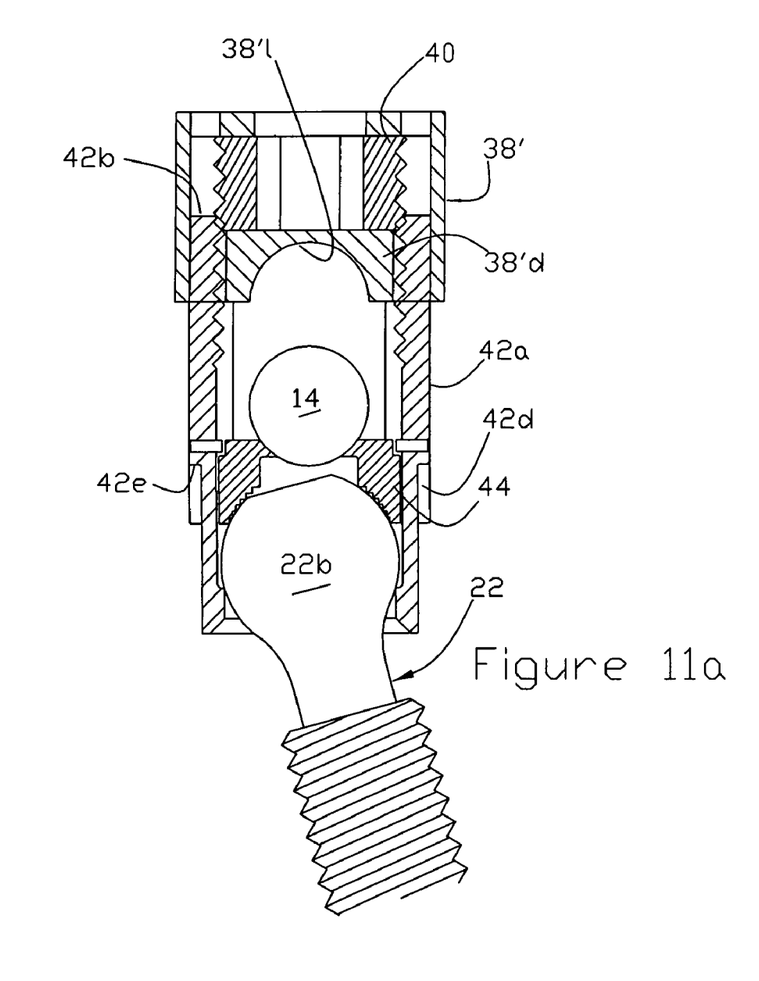
FIGS. 11a and 11b are cross-sectional views of the modified cap/set screw design of FIGS. 10a and 10b being installed on the housing of a polyaxial pedicle screw implant.
Figure 11B:
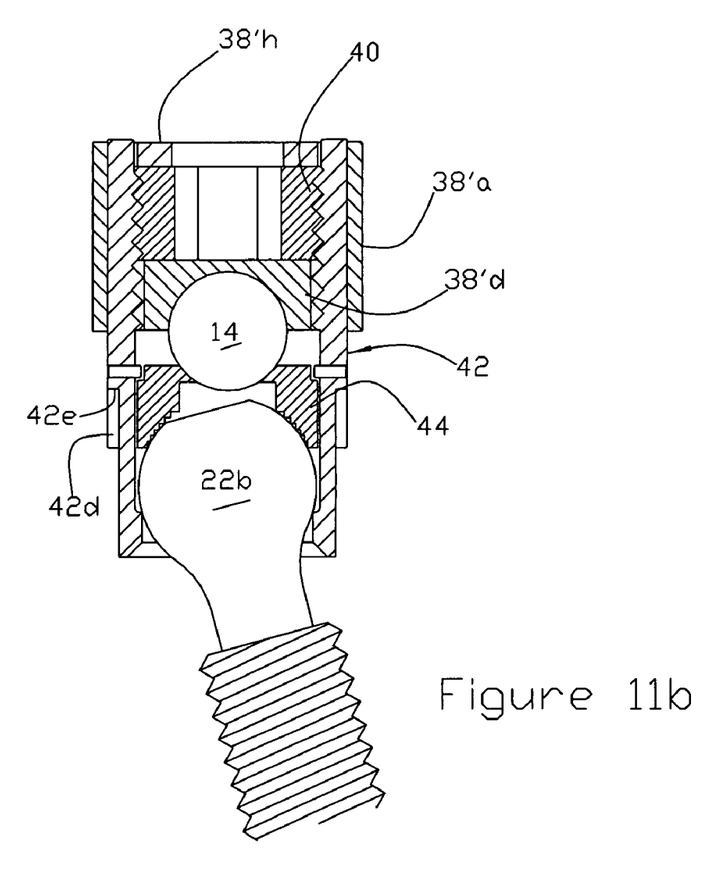

FIGS. 11a and 11b illustrate the use of the cap/set screw of FIG. 10 with the polyaxial pedicle screw housing 42 of FIG. 8. As is illustrated in FIG. 11b, the lower surface 38'l of the bottom strut 38'd (instead of the bottom of the set screw) is forced against the top of the rod 14 to lock the implant, rod and bone screw 22 together. The uninterrupted bottom strut 38'd provides a smoother surface against which the set screw rotates and also provides a greater downward force per axial rotation. This is beneficial in locking the polyaxial pedicle screw to the rod. See FIG. 11b. This additional downward force, while advantageous for polyaxial systems, is not needed for the monoaxial screws or hooks and thus the set screw is allowed to contact the rod directly reducing the overall height of the top of the monoaxial screw or hook.

Figure 12A:
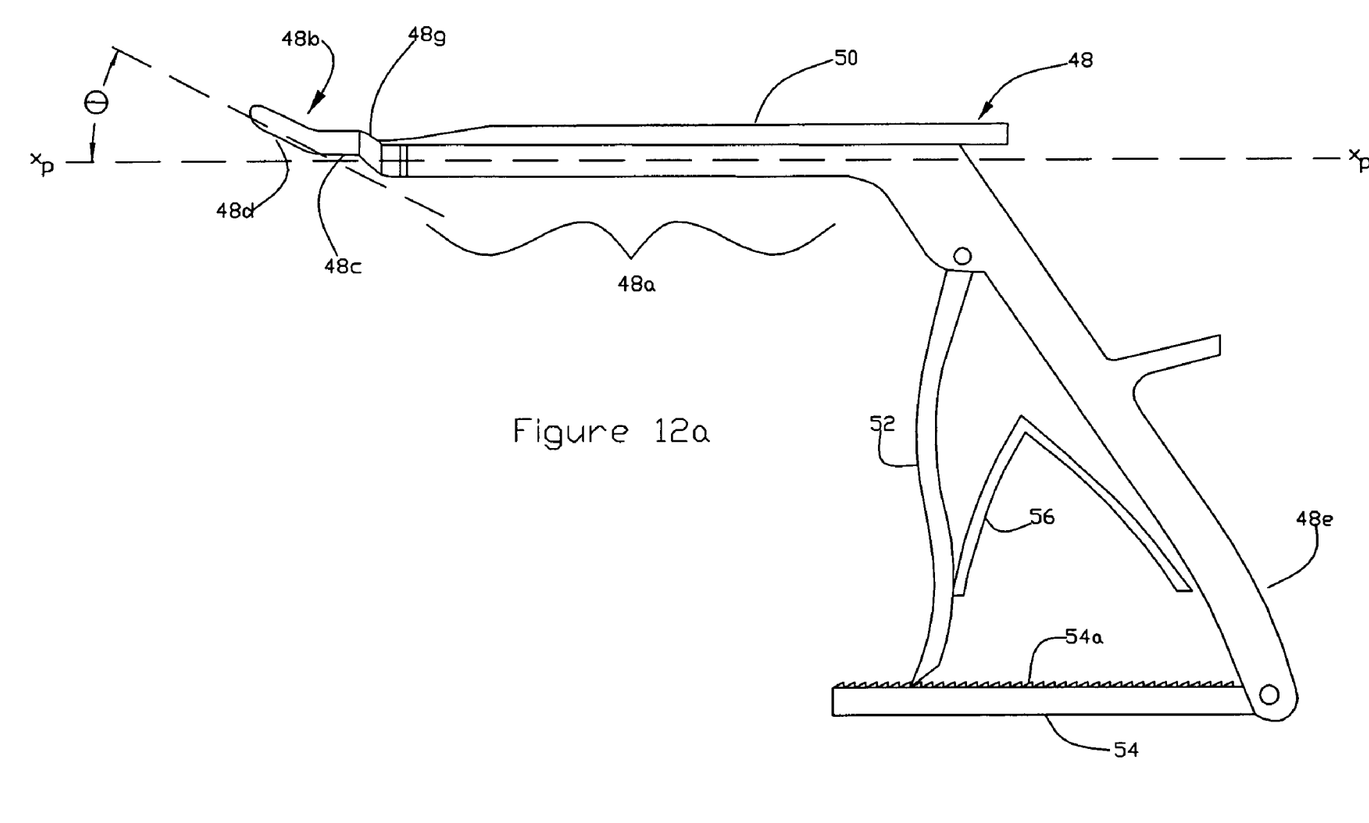
FIGS. 12a and 12b are side elevational and top plan views of a rod persuasion instrument or persuader.
Figure 12B:
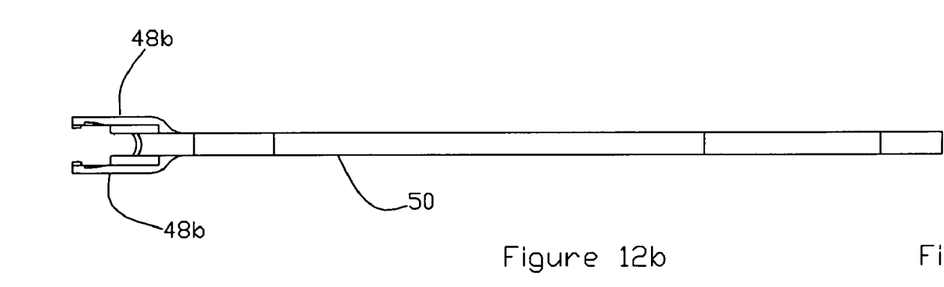
Figure 12C:
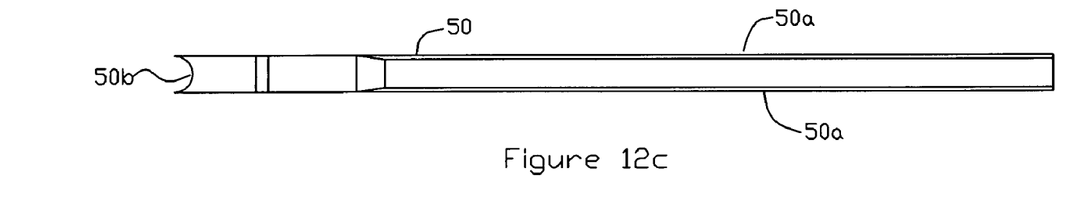
FIGS. 12c and 12d are top plan and side elevational views of a rod pusher bar forming a part of the persuader.
Figure 12D:
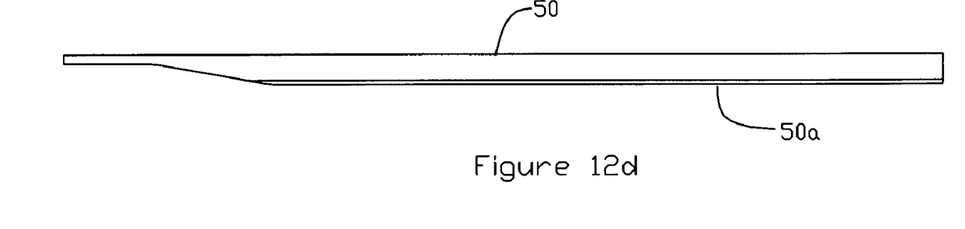
Figure 12E:
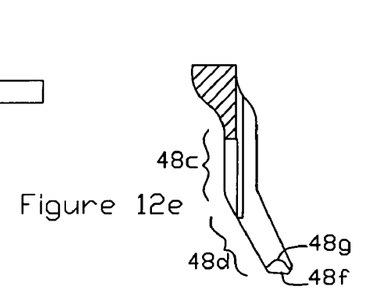
FIGS. 12e and 12f are side elevational (partially in section) and top plan views of the tip of the persuader for engaging the catch basin of an implant.
Figure 12F:
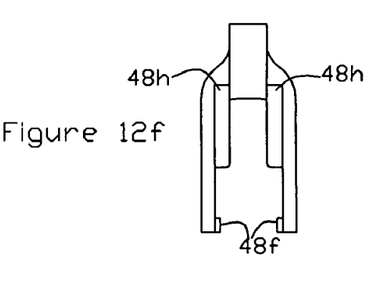

A rod persuasion instrument or persuader 48 (made, for example of stainless steel), for use with the catch basin described above, is illustrated in FIGS. 12a-12g. The persuader includes a carriage, in the form of an elongated member 48a, extending along a longitudinal axis Xp-Xp with branched parallel arms 48b having a short horizontal section 48c extending from the distal end 48g of the elongated member and an offset section 48d extending at an acute angle θ to the longitudinal axis as is shown in FIGS. 12a and 12g. The carriage further includes an integrally formed handle 48e. Inwardly extending short (e.g., 1 mm in length) stubs or buttons 48f (FIG. 12f) are provided at the terminal ends of the offset arms 48d with the distance between the stubs being slightly greater, e.g., 0.001" to 0.003", than the width $W_{BC}$ (FIG. 8b) of the catch basin on the implant upper section or housing. The catch basin engaging stubs are formed with convex semi-cylindrical surfaces 48g facing the proximal end of the carriage, as is best shown in FIG. 12e. Spaced parallel rod pusher guides 48h are formed along inner portions of the horizontal section 48c.

A rod pusher bar 50 (FIGS. 12c-12d) is slidably mounted in the elongated member of the carriage via lateral tongues 50a which slide into cooperating grooves in the carriage (not shown). The distal end of the pusher bar rides between carriage guides 48h and is formed with a concave end 50b, e.g., sector of a circle, which is arranged to engage a stabilizer rod when stubs 48f are seated in the catch basin of an implant and the pusher bar is advanced toward the rod via a pivotally mounted actuating trigger 52 in a conventional manner. A base 54 is pivotally mounted to the end of the handle 48e and has a serrated upper side 54a which is biased against the free end of the trigger. A spring 56 biases the trigger away from the handle. The surgeon may advance the pusher bar by pulling the trigger toward the handle and it will remain in the deployed position until the base 54 is manually rotated away from the trigger to withdraw the bar to its stored position as will be obvious to those skilled in the art.

It is to be noted that the arms 48b may extend to the distal end of the carriage eliminating the need for the horizontal section 48c. Also, the angle θ may vary within the range of 0° to about 45°, but preferably is within the range of about 15° to 30°. It has been found that an angle θ of about 25° functions quite well.

Figure 13A:
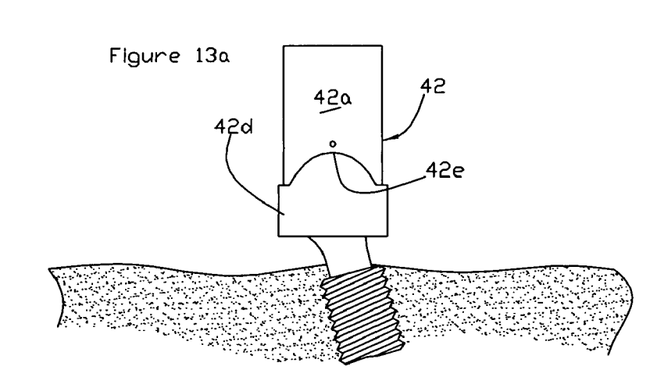
FIGS. 13a, 13b and 13c are diagrammatic views showing the use of the rod persuader of FIG. 12 to seat a stabilizing rod in the implant rod receiving opening.
Figure 13B:
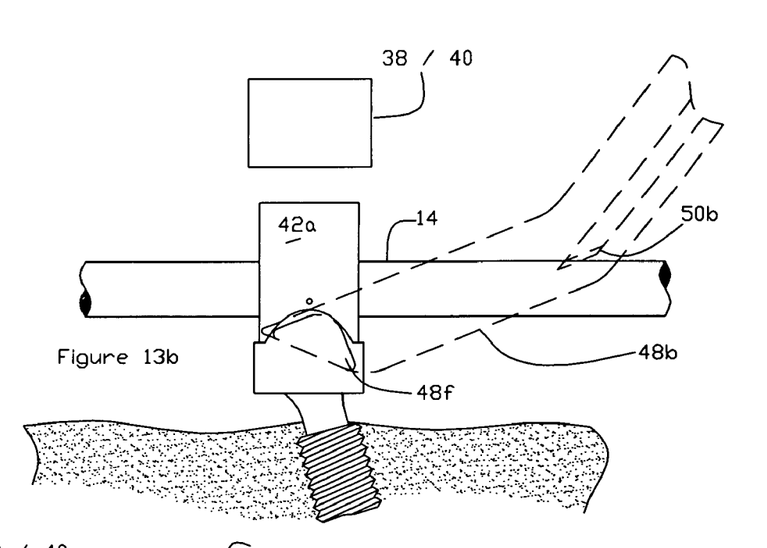
Figure 13C:
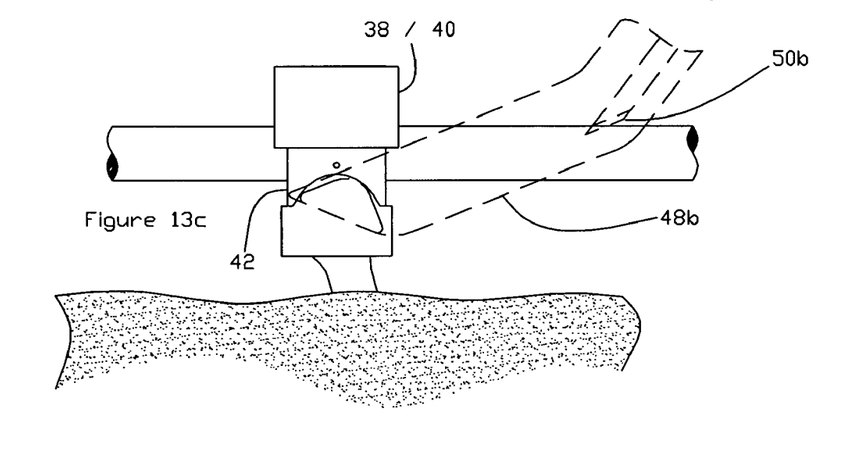

FIGS. 13a-13c illustrate, in diagrammatic form, the use of the persuader of FIGS. 12a-12f to force a stabilizing rod 14 within the rod receiving opening between posts of a polyaxial pedicle screw implant. FIG. 13a illustrates a polyaxial pedicle screw installed into an underlying bone segment with the housing free to be aligned with the anticipated position of a stabilizing rod in a conventional manner. FIG. 13b illustrates one of the persuader offset arms 48b extending around the lower portion of one side wall 42a of the housing 42 with one of the catch basin engaging stubs 48f engaging the concave shoulder 42e to fix the distal end of the persuader relative to the housing. The other stub would be in engagement with the concave shoulder on the other side of the housing. The rod engaging end of the pusher bar has been moved forwardly to seat the rod between the housing posts. FIG. 13c shows the cap/set screw installed in the housing with the persuader still in place.

Figure 14:
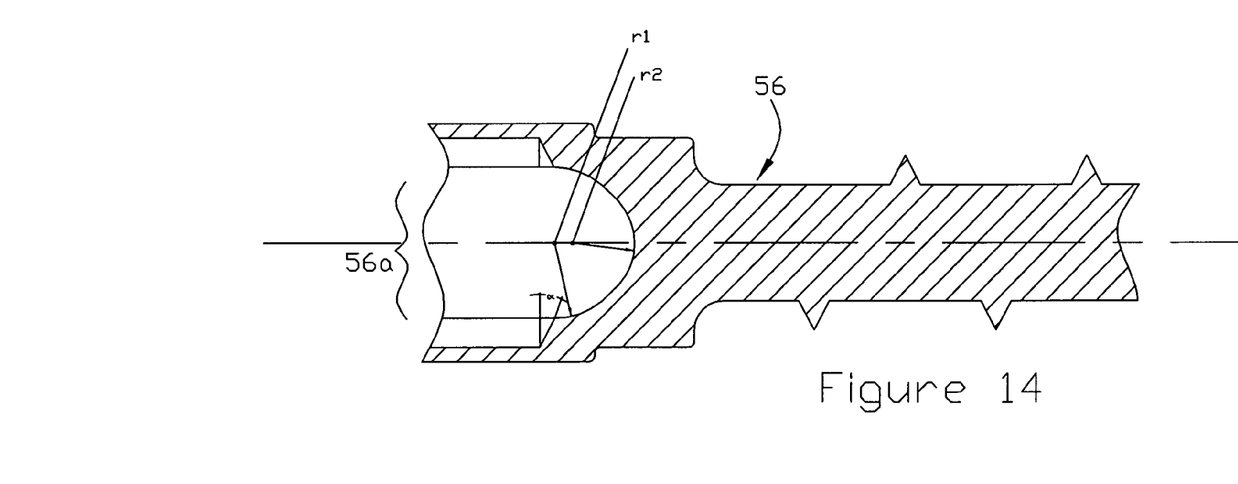
FIG. 14 is a cross-sectional view of the rod receiving opening of a hook or monoaxial pedicle screw implant in accordance with the features of the invention for accommodating stabilizing rods of different diameters.

FIG. 14 illustrates another aspect of the invention for the rod receiving portion (i.e., cradle) of a monoaxial pedicle screw or hook implant. The rod receiving portion 56a of the monoaxial pedicle screw 56 shown in FIG. 14 is sized to accept a spinal rod of two different diameters of rods, e.g., 0.216" and 0.250" diameters. The lower portion of the cradle is provided with a smaller radius r2, e.g., 0.1080" to capture the smaller rod while the upper portion of the cradle is provided with a larger radius r1, e.g., 0.130" to capture the larger rod.

There has thus been described a novel integrally formed cap/set screw for use with vertebral implants having upstanding internally threaded posts along with additional implant features enhancing the reliability and user friendliness of the implant system. The details and parameters of the present invention may be altered in numerous ways without departing from the spirit and scope of the invention as defined in the appended claims. Therefore, it is intended that the drawing be interpreted as illustrative and not in any way viewed as being a limitation on the invention.

What is claimed is:

1. An implant system for use with a stabilizing rod for immobilizing bone segments comprising:
   a) an implant adapted to be secured to a bone segment, the implant having a longitudinal axis and a pair of upstanding internally threaded implant posts extending parallel to the longitudinal axis and defining a transverse opening for receiving a stabilizing rod, the implant posts having curved outside surfaces,
   b) a cap with opposed curved side walls which extend around the implant posts and end walls extending between the side walls, the cap having integral top and bottom struts, extending across a hollow opening, with a fixed distance there between;
   c) a set screw rotatably mounted within the cap and aligned between the side walls and the top and bottom struts, for positioning between the implant posts, the set screw having a top defining a wrench engaging surface and external threads arranged to engage the internally threaded implant posts whereby rotation of the set screw will advance the cap and set screw in unison along the implant posts to fix the stabilizing rod, the cap having coaxial alignment means in cooperation with the implant posts to coaxially align the set screw with the implant longitudinal axis and prevent the cap from rotating relative to the implant posts, the set screw has a bottom surface that rotates above the bottom strut to force a lower surface of the cap to directly contact and apply a fixation force on the stabilizing rod.

2. The implant system of claim 1 wherein the implant is in the form of a polyaxial pedicle screw.

3. The implant system of claim 1 wherein the implant posts have free edges and wherein the coaxial alignment means includes means on the cap for cooperating with the implant posts free edges for preventing the rotational movement of the cap.

4. The implant system of claim 3 wherein the set screw has a lower surface, exterior cap end walls that are substantially flat and wherein the means for coaxially aligning the set screw with the implant longitudinal axis includes the bottom strut and the top strut extending between the end walls with the struts and side walls forming diametrically opposed openings which slide over the implant posts, the struts permanently encapsulating the set screw within the cap with the set screw offset by approximately 0.0005 to 0.010 inches from an interior of the cap and walls.

5. The implant system of claim 4 wherein a difference in length lc of diametrically opposed openings in the cap and a width Wp of the implant posts is within a range of 0.001" to 0.020".

6. The implant system of claim 5 wherein the cap end walls define upwardly extending aligned concave curved surfaces which generally follow the contour of the rod.

7. The implant system of claim 6 wherein said bottom strut forms a concave rod-engaging surface which extends between the end walls so that when the set screw is advanced along the implant posts the bottom strut concave rod-engaging surface engages the stabilizing rod.

8. The implant system of claim 6 wherein each of the cap end walls define a curved concave surface following the contour of an upper surface of the stabilizing rod extending upwardly from the bottom of the end wall and wherein said bottom strut comprises two opposed struts extending between the end walls with the two opposed struts being arranged to allow the bottom surface of the set screw to engage the stabilizing rod.

9. The implant system of claim 1 wherein an implant upper section includes a persuader tip catch basin formed with parallel flat recessed sides on side walls which extend upwardly to respective concave outwardly projecting shoulders with a depth of the shoulders being within a range of about 0.5 mm to 3 mm.

10. An implant system for use with a rod for immobilizing bone segments comprising:
   a) an implant adapted to be secured to a bone segment and having a pair of upstanding internally threaded posts defining a transverse opening for receiving a rod; and
   b) an integrally formed cap and set screw defining diametrically opposed openings which slide over the posts of the implant with the openings extending through the cap, the cap including a top strut and a bottom strut integrally fixed at a set distance within the cap and extending across a hollow opening between which the set screw is encased, the set screw being free to rotate within the cap, the set screw having external threads arranged to engage the upstanding internally threaded posts and a wrench engaging surface accessible at the top of the set screw whereby the cap and set screw are integrally advanced in unison along the upstanding internally threaded posts, a lower portion of the cap or set screw being arranged to engage the rod to clamp a rod and implant together.

11. The implant system of claim 10 wherein the implant is in the form of a polyaxial pedicle screw.

12. The implant system of claim 11 wherein the polyaxial pedicle screw comprises a pedicle screw having an enlarged head retained within a polyaxial housing via a floating pressure washer disposed above the screw head, and restricted in vertical movement within the polyaxial housing to hold the pedicle screw, pressure washer and polyaxial housing together, the lower section of the cap or set screw being arranged to force the rod against the pressure washer to clamp the rod and implant together.

13. The implant system of claim 12 wherein the pressure washer is made of a cobalt alloy.

14. The implant system of claim 10 wherein the implant posts have outside surfaces and wherein the cap is formed with side walls having curved inside surfaces which follow a contour of the posts' outside surfaces and substantially flat end walls with the top strut extending between the end walls and above the bottom strut extending between the end walls and below the set screw, the struts and end walls encapsulating the set screw within the cap, the top strut defining an opening through which a wrench may be inserted into the wrench engaging surface of the set screw.

15. The implant system of claim 14 wherein inner surfaces of the end walls follow a contour of the set screw to align the set screw with a longitudinal axis of the cap.

16. The implant system of claim 15 wherein the cap end walls define upwardly extending aligned concave curved surfaces which generally follow a contour of the rod.

17. The implant system of claim 16 wherein said bottom strut forms a solid longitudinal concave rod-engaging surface which extends between the end walls so that when the set screw is rotatably advanced along the implant posts the bottom strut engages the top of the rod with the diametrically opposed openings on either side of the bottom strut.

18. The implant system of claim 16 wherein each of the caps' end walls defines a curved concave surface following a contour of an upper surface of the rod extending upwardly from a bottom of the end walls and wherein said at least one bottom strut comprises two opposed struts extending between the end wall with the lower struts being arranged to allow a bottom of the set screw to engage the rod.

19. An implant system for immobilizing bone segments comprising:
   a) a stabilizing rod;
   b) an implant adapted to be secured to a bone segment and having a pair of upstanding internally threaded arcuate posts defining a transverse opening for receiving the rod;
   c) a cap having opposed curved side walls which extend around the posts and substantially flat end walls extending between the side walls and the end walls defining upwardly extending concave semicircular openings following a contour of a rod outside surface, the cap further having an integral top and bottom struts, extending across a hollow opening, and defining opposed openings extending through the cap adjacent the end walls for receiving the implant posts; and
   d) a set screw rotatably mounted in the cap, between the top and bottom struts, and positioned within the posts, the set screw having a top defining a wrench engaging surface, a bottom and external threads arranged to engage the threaded arcuate posts, whereby rotation of the set screw will advance the cap and set screw in unison along the implant, the bottom strut of the cap being arranged to engage the rod to clamp the rod and implant together.

20. A implant assembly for use with a stabilizing rod for immobilizing bone segments comprising;
   a) a pedicle screw having a threaded shaft for insertion into a bone segment and an enlarged generally spherical head;
   b) a polyaxial housing having a bore with a longitudinal axis therethrough, for accommodating the passage of the threaded shaft therethrough, an upper portion of the housing including a pair of internally threaded opposed posts defining an opening substantially perpendicular to the bore axis for receiving a stabilizing rod, the housing terminating at its lower end in a reduced cross-sectional area for engaging the bottom of the screw head to retain the screw head within the housing; and
   c) an integrally formed cap with a hollow opening and a set screw arranged along the longitudinal axis, the cap defining diametrically opposed openings extending therethrough which slide over the posts of the polyaxial housing, the cap having a top strut and a bottom strut, extending across a hollow opening, at a fixed longitudinal distance from each other, the set screw is encased in the hollow opening between the top strut and the bottom strut, the set screw being free to rotate relative to the cap and having external threads arranged to engage the pair of threaded opposed posts of the polyaxial housing, the cap further having a wrench engaging surface disposed along the longitudinal axis whereby the cap and set screw can be advanced in unison along the polyaxial housing, a lower section of the cap or the set screw being arranged to engage the rod to clamp the rod and implant assembly together.

21. The implant assembly of claim 20 wherein the cap and top and bottom struts are formed of titanium and a pressure washer of a CoCrMo alloy is secured within the polyaxial housing to capture the pedicle screw within the polyaxial housing, the pressure washer has limited movement and is configured to be forced into a fixing engagement to hold the enlarged generally spherical head in a desired alignment relative to the longitudinal axis of the polyaxial housing when the rod and implant assembly are clamped together.

22. The implant assembly of claim 21 wherein the pressure washer has surface slots for penetrating into the enlarged generally spherical head for locking the pressure washer to the spherical head.

23. The implant assembly of claim 22, wherein the spherical head is formed of titanium with a Rockwell C hardness value of around 35 and the pressure washer has a Rockwell C hardness value of around 43.

24. An implant system for immobilizing spinal bone segments comprising:
   a) an elongated stabilizing rod; and
   b) a two component implant assembly for attaching a bone segment to the stabilizing rod, each component having self contained parts to enable a surgeon to attach the components during surgery, including;
      (1) a pedicle screw and polyaxial housing component, the pedicle screw having a threaded shaft for insertion into a spinal bone segment and an enlarged generally spherical head and the polyaxial housing having a bore with a longitudinal axis therethrough, for accommodating the passage of the threaded shaft therethrough, an upper portion of the polyaxial housing including a pair of internally threaded opposed posts defining an opening substantially perpendicular to the bore axis for receiving a stabilizing rod, the polyaxial housing terminating at its lower end in a reduced cross-sectional area for engaging a bottom of the screw head to retain the screw head within the polyaxial housing, a pressure washer of a CoCrMo alloy is secured within the polyaxial housing to capture the pedicle screw within the polyaxial housing, the pressure washer has limited movement and is configured to be forced into a fixing engagement to hold the enlarged generally spherical head in a desired alignment relative to the longitudinal axis of the polyaxial housing when the rod and implant assembly are clamped together, and (2) an integrally formed titanium cap with a hollow opening and a set screw arranged along the longitudinal axis, the cap defining diametrically opposed openings extending therethrough, which slide over the posts of the polyaxial housing, the cap having a top strut and a bottom strut extending across the hollow opening and offset at a fixed longitudinal distance from each other, the set screw encased between the top strut and the bottom strut, the set screw being free to rotate relative to the cap and having external threads arranged to engage the pair of internally threaded opposed posts, the cap further having a wrench engaging surface disposed along the longitudinal axis whereby the cap and set screw can be advanced in unison along the polyaxial housing, a lower section of the cap or the set screw being arranged to engage the rod to clamp the rod and implant assembly together.

25. The implant system of claim 24 wherein the set screw has a bottom surface that rotates on top of the bottom strut and the bottom strut has a lower surface with a concave rod-engaging surface, the cap has diametrically opposed end walls with exterior flat surfaces that connect to either side of the bottom strut.

26. The implant system of claim 25 wherein the pressure washer has a concave lower surface with a plurality of raised ridges configured to ensure a locking co-action with the generally spherical screw head, wherein the set screw is offset by approximately 0.005 to 0.010 inches from an interior of the end walls of the cap, the sides of the bottom strut defining with the corresponding sides of the cap diametrically opposed openings dimensioned to receive respectively, the pair of internally threaded opposed posts, wherein the differences in length of the semi-circular openings and the widths of the thread opposed posts is within a range of 0.001 to 0.20 inches to ensure a precise alignment of the set screw and the threaded opposed posts.

* * * * *